United States Patent
Ginn

(10) Patent No.: US 7,647,930 B2
(45) Date of Patent: Jan. 19, 2010

(54) FALLOPIAN TUBE OCCLUSION DEVICES AND METHODS

(75) Inventor: Richard S. Ginn, Gilroy, CA (US)

(73) Assignee: Promed, Inc., Gilroy, CA (US)

( * ) Notice: Subject to any disclaimer, the term of this patent is extended or adjusted under 35 U.S.C. 154(b) by 11 days.

(21) Appl. No.: 11/833,182

(22) Filed: Aug. 2, 2007

(65) Prior Publication Data

US 2008/0066763 A1    Mar. 20, 2008

Related U.S. Application Data

(60) Provisional application No. 60/821,238, filed on Aug. 2, 2006.

(51) Int. Cl.
*A61F 6/06* (2006.01)
*A61B 17/00* (2006.01)

(52) U.S. Cl. .................. 128/831; 128/830; 128/887; 606/198; 604/15

(58) Field of Classification Search .......... 128/830, 128/831, 832, 836, 887; 606/153, 193, 197, 606/198, 199, 213, 215, 216; 623/1.11, 1.12; 600/32, 184; 604/15, 16, 17, 18, 164.03, 604/164.04, 164.12

See application file for complete search history.

(56) References Cited

U.S. PATENT DOCUMENTS

| 3,397,699 | A  | * | 8/1968 | Kohl ........................... 604/105 |
| 4,677,967 | A  | * | 7/1987 | Zartman ...................... 128/830 |
| 5,935,137 | A  | * | 8/1999 | Saadat et al. ................. 606/135 |
| 6,705,323 | B1 | * | 3/2004 | Nikolchev et al. ........... 128/830 |
| 6,763,833 | B1 |   | 7/2004 | Khera et al. |
| 6,780,197 | B2 | * | 8/2004 | Roe et al. .................... 606/213 |
| 6,871,650 | B1 |   | 3/2005 | Nikolchev et al. |
| 7,220,259 | B2 |   | 5/2007 | Harrington |
| 2005/0172972 | A1 | | 8/2005 | Nikolchev et al. |
| 2008/0060658 | A1 | * | 3/2008 | Doorschodt ................. 128/831 |

* cited by examiner

*Primary Examiner*—Patricia M Bianco
*Assistant Examiner*—Victoria Hicks
(74) *Attorney, Agent, or Firm*—Orrick, Herrington & Sutcliffe LLP

(57) ABSTRACT

Occlusion devices and methods for occluding fallopian tubes which take effect promptly after deployment. The occlusion device comprises an occluding element and a fixation element. In one embodiment, the occluding element is deployed within the fallopian tube and in another embodiment, the occluding element is external to the fallopian tube.

8 Claims, 8 Drawing Sheets

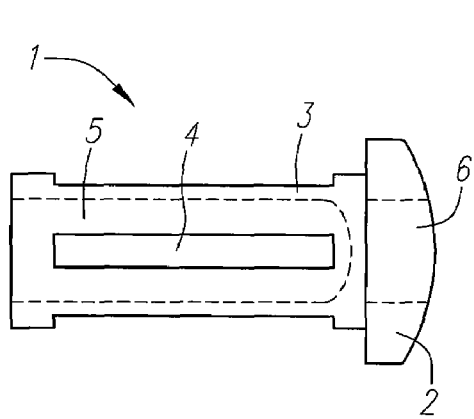
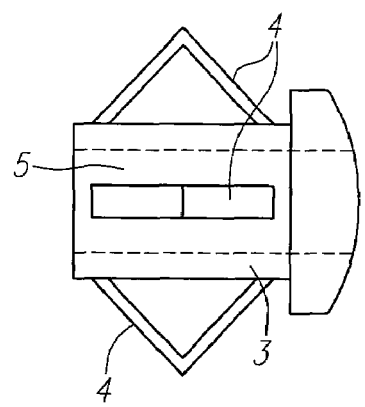
FIG. 1        FIG. 2
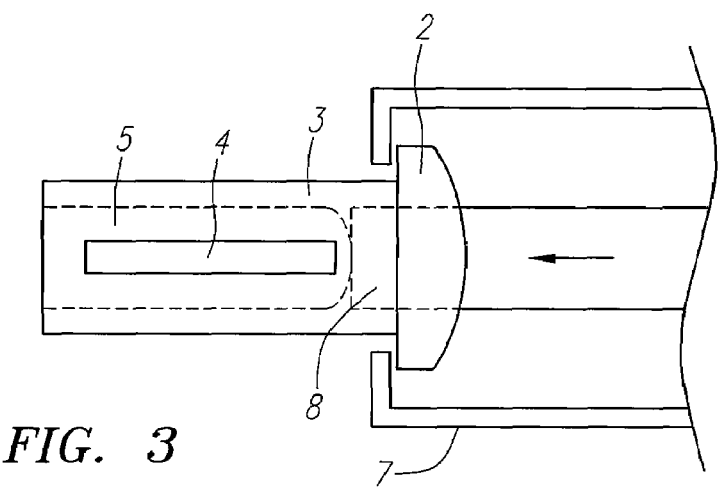
FIG. 3
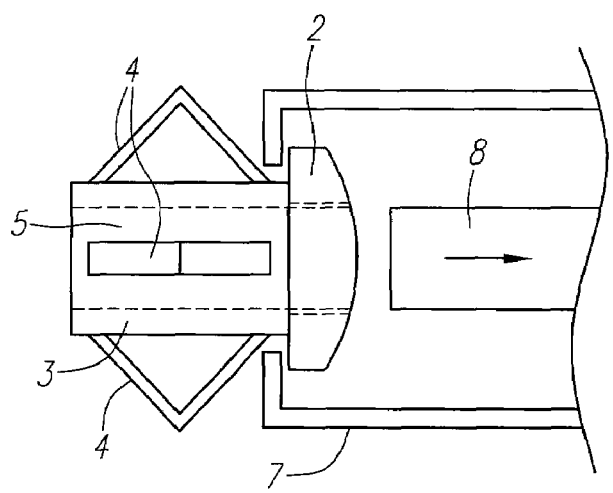
FIG. 4

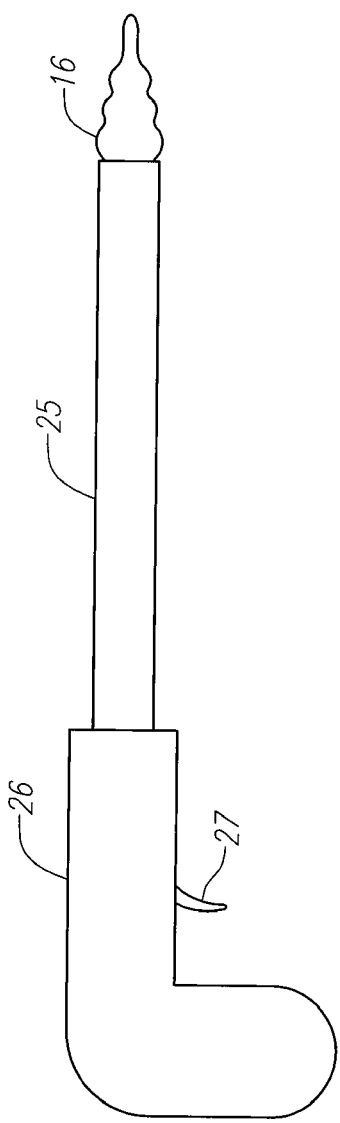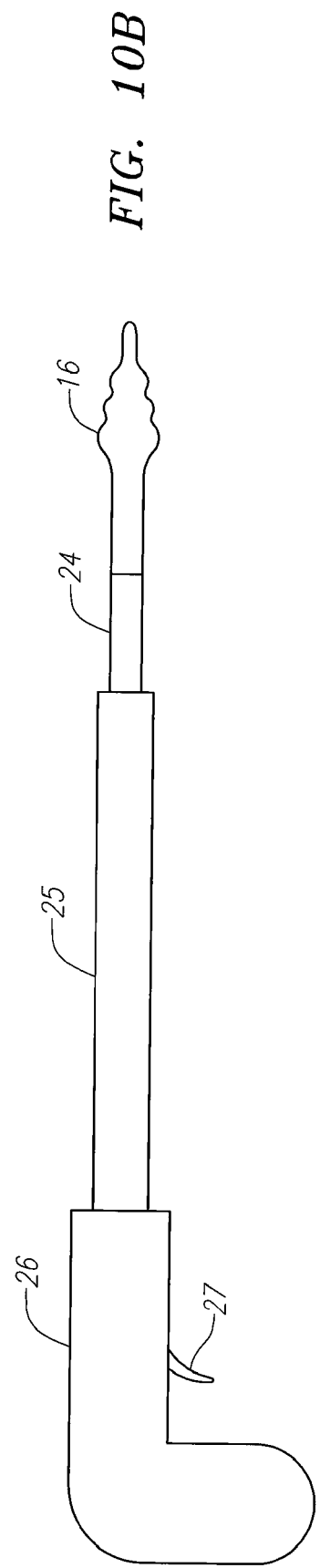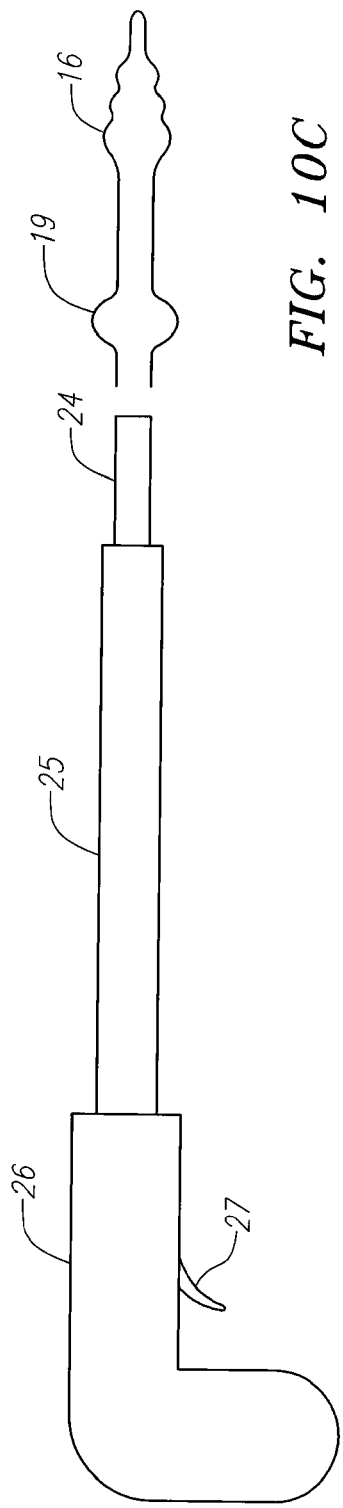

FALLOPIAN TUBE OCCLUSION DEVICES AND METHODS

CROSS-REFERENCE TO RELATED INFORMATION

The application claims priority to U.S. provisional patent application Ser. No. 60/821,238 filed on Aug. 2, 2006, which is fully incorporated herein by reference.

BACKGROUND OF THE INVENTION

The present invention relates generally to contraception, and more particularly, to intrafallopian contraceptive devices and non-surgical methods for their delivery.

The art to which the present invention is directed is described in United State Published Patent Application No. 2005/0172972, the entirety of which is incorporated herein by reference.

SUMMARY OF THE INVENTION

The device of the present invention comprises a cap and a body. The body is provided with expandable attachment means which collapse when the device is placed under axial stress. When the stress is removed, the compressed attachment means expand. The device can be used to occlude the fallopian tube without perforating it.

The device, and its deployment in this manner, achieve virtually instant sterilization.

DESCRIPTION OF THE DRAWINGS

FIGS. 1 and 2 show the occluder without a delivery device with the body in the extended, stressed condition in FIG. 1 and in the unstressed shortened condition in FIG. 2.

FIGS. 3 and 4 show the occluder device in combination with the deployment device, with the attachment means collapsed in FIG. 3 and expanded in FIG. 4.

FIGS. 10A-C are sequential illustrations which show the several stages of deployment of the occlusion device.

DETAILED DESCRIPTION OF THE INVENTION

Figure 5:
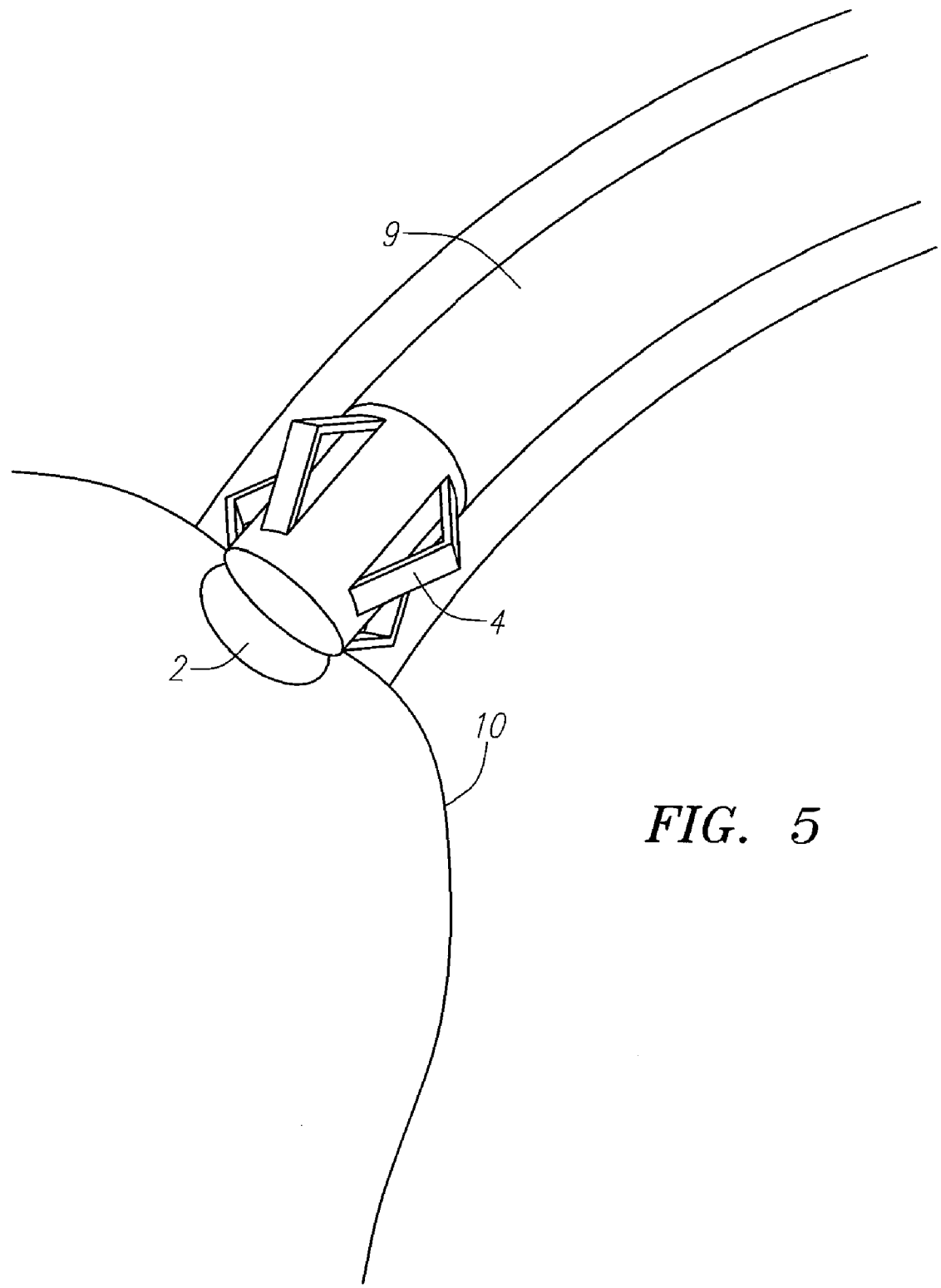
FIG. 5 shows the device after installation in the fallopian tube.

As shown in FIG. 1, the occluder 1 comprises a cap 2, a body 3, attachment device 4 and plug 5. Cap 2 is provided with through hole 6. As shown, the body is in an extended, stressed condition and expansion means 4 is in a collapsed condition.

FIG. 2 shows occluder 1 with attachment means 4 in their expanded configuration after the lengthening stress on body 3 has been removed.

As can be seen in a comparison of FIG. 2 with FIG. 1, the lengthening of body 3 is accomplished by exerting axial force on plug 5. When that force is removed, plug 5 assumes its unstressed shorter configuration as shown in FIG. 2 and plug 5 moves into through hole 6 such that there is no longer an opening in cap 2. The body 3 may be made of nitinol metal while cap 2 and plug 5 may be made from a suitable polymer material.

FIG. 3 shows the occluder in combination with a delivery means comprising grasper 7 and plunger 8. In the configuration shown in FIG. 3, plunger 8 pushes on plug 5 to cause the body 3 to assume its extended, stressed configuration and causes grasper 7 to engage cap 2.

As shown in FIG. 4, when plunger 8 is retracted, body 3 shortens and attachment members 4 assume their expanded configuration. This shortening of body 3 moves plug 5 into the through hole 6 in cap 2.

FIG. 5 shows the occluder device after installation with attachment means 4 engaging the wall of fallopian tube 9 and cap 2 sealing the fallopian tube at uterus wall 10. Once deployed, the device achieves virtually instant sterilization.

Figure 6:
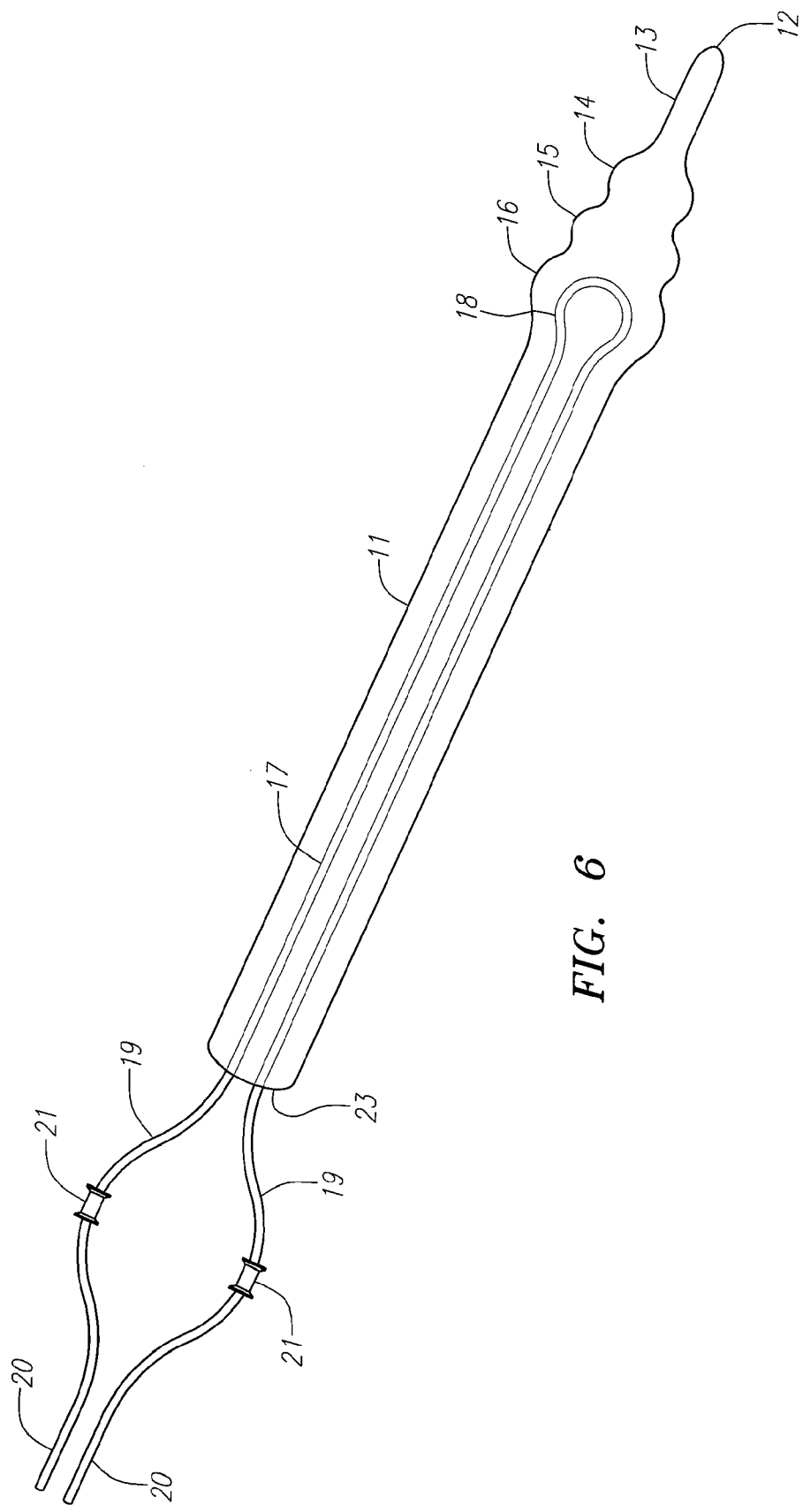
FIG. 6 shows an alternate embodiment of the occlusion device of the present invention which comprises an occluder element and a fixation element in which the fixation element comprises a looped wire.

An alternate embodiment of the occluder device of the present invention is shown in FIG. 6. In this embodiment, the occluder device has a distal portion which is the occluder element and a proximal portion which is the fixation element. The occluder element comprises a tubular portion 11 which is preferably fabricated from a soft polymeric or elastomeric material which has a distal end region 12 with a relatively narrow diameter. Located proximally to the distal region 12 are a series of spaced ribs 13-16 which have progressively increasing diameters. The portion of the occluder element extending from the narrow diameter tip to the largest diameter rib 16 may be hollow or solid. The number of ribs shown in FIG. 6 is exemplary only and there may be a lesser or greater number of ribs. Each of the ribs plays a role in occluding a fallopian tube, but the largest diameter rib is the primary occluding element. A fixation element 17 which has a distal portion 18 and a proximal portion 19 extends from a point proximal to the proximal end of the occlusion element 11 to a point in the region of the distal end of the occluding element, typically in the region of ridge 16. The distal end 18 of the fixation element may comprise an enlarged loop as shown in FIG. 6 or may have any other suitable configuration. A proximal portion 19 of the fixation element 17 preferably bows outwardly as shown in FIG. 6 with a straight portion 20 proximal to the bowed portion 19. As will be described in more detail below, the bowed portion 19 of the fixation element is fabricated from a resilient or elastic material which can be deformed such that it is in alignment with straight portions 20 when constrained by a sleeve (not shown) and which will revert to its bowed configuration when the constraint is removed as shown in FIG. 6. Optionally, a tissue-engaging element 21 can be attached to the bowed portions 19. For example, the fixation device may have the configuration of a flared cylinder as shown in FIG. 6 or it can have other configurations such as a barb, hook, or other projection including the type shown as element 4 in FIG. 2 hereof.

Figure 7:
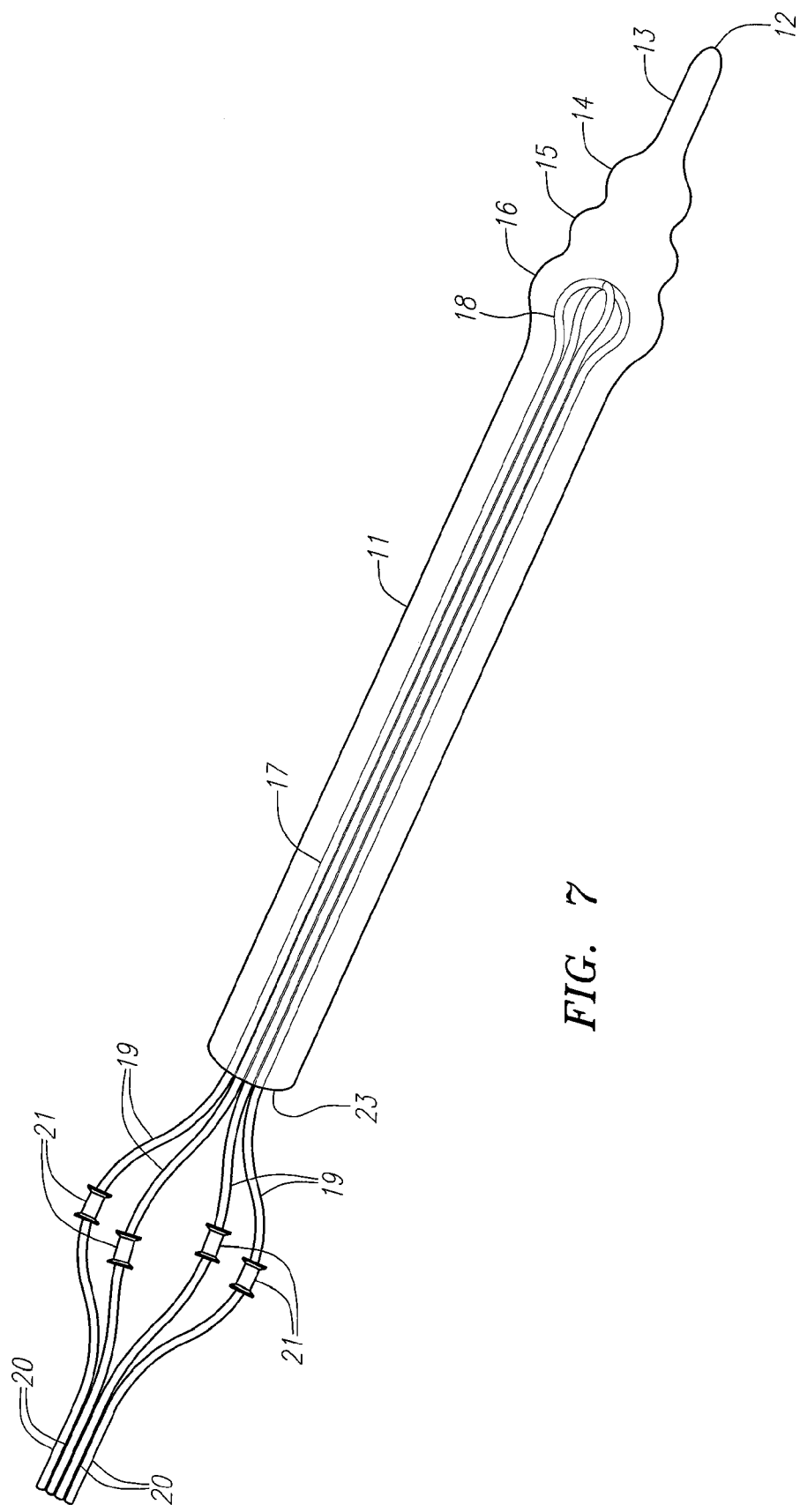
FIG. 7 shows a variation of the embodiment of FIG. 6 in which the fixation element comprises two looped wires.

FIG. 7 illustrates an occlusion device similar to that illustrated in FIG. 6 and the same reference numerals are used for the same elements. However, in FIG. 7, the illustrated embodiment has a fixation element comprising two looped wires rather than one looped wire as shown in FIG. 6.

Figure 8:
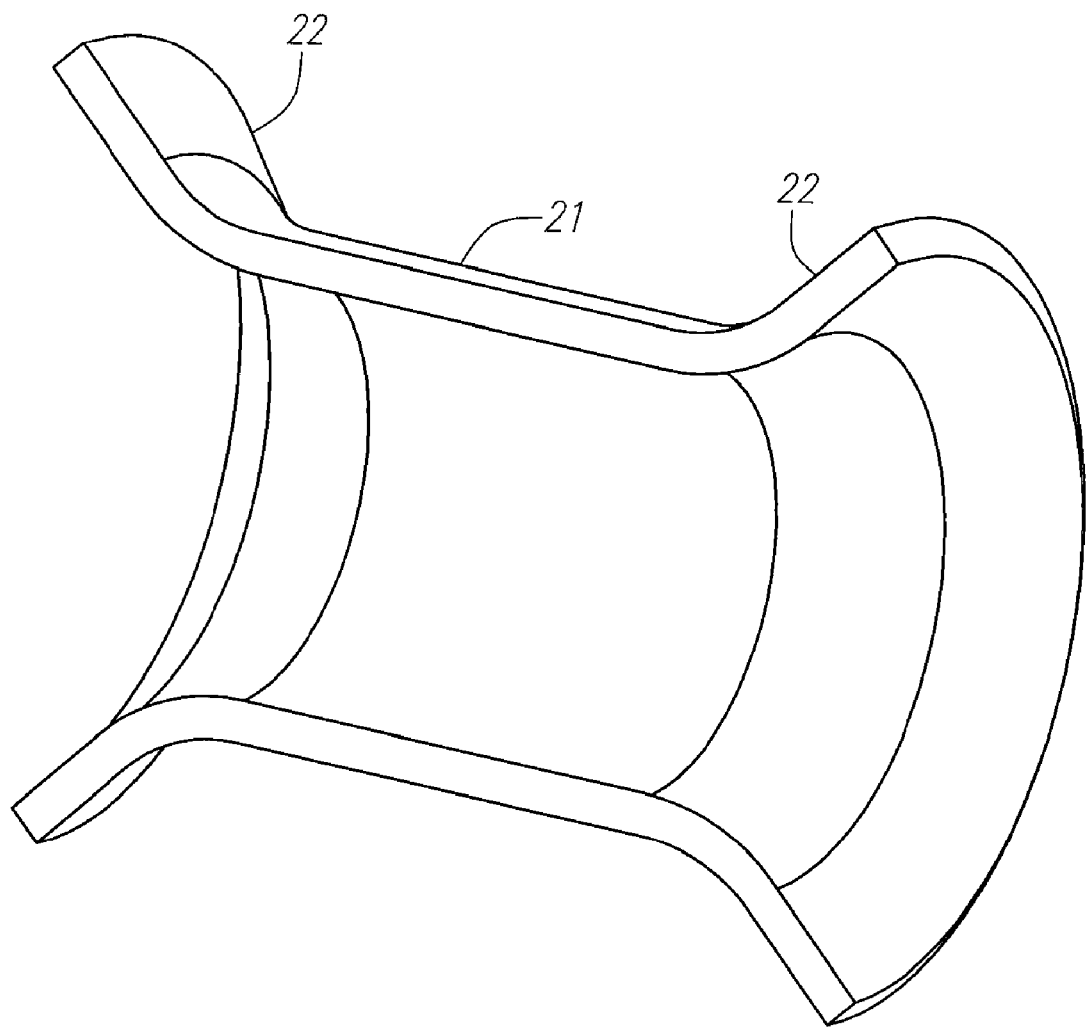
FIG. 8 shows a fixation enhancing attachment which may be added to the fixation element.

FIG. 8 is a cross-sectional view of fixation enhancing attachment 21 which has flared ends 22.

Deployment of the occlusion devices of FIGS. 6 and 7 is accomplished by using a delivery device comprising two sleeves, an inner sleeve or tube which abuts the proximal end of occlusion element 11 and which constrains the bowed portions 19 of fixation element 17 such that they are aligned with proximal portions 20. A second outer sleeve or tube is positioned over occlusion element 11 and over the inner sleeve such that the distal end of the outer sleeve abuts the largest diameter rib 16. The outer sleeve is attached to a handle and is flexible. Preferably, the occlusion device is deployed in conjunction with the use of a hysteroscope which permits visualization of the target fallopian tube and which has a separate lumen adapted for delivery of the occlusion device. Thus, by first visualizing the fallopian tube and then manipulating the handle attached to the outer tube of delivery device, the occlusion device can be inserted into the fallopian tube such that, preferably, the insertion is deep enough for the proximal end 20 of the fixation device to be located within the fallopian tube. The outer and inner tubes are then removed such that the outer tube no longer contacts the occlusion device and such that the bowed portions 19 of the fixation element 17 are free to bow outwardly into contact with the tissue of the fallopian tube. If the optional fixation elements 21 are used, they will also be brought into contact with the tissue of the fallopian tube.

As with the device shown in FIGS. 1-5, the occlusion device of FIGS. 6 and 7 will immediately occlude the fallopian tube such that the waiting time associated with other fallopian tube occluders before they are effective in occluding a fallopian tube is not required.

The fixation element 17 can be made out of any suitable resilient or elastic material which may be either metal or polymeric, e.g., metals such as nitinol, stainless steel, plastic, reinforced plastics or other suitable materials may be used. Among the polymeric materials which may be used are included polyimides, polyolefins, polycarbonates, polyesters, polyamides, polyurethanes, synthetic rubbers, etc. Similarly, the occlusion element can be made from a wide variety of materials. Preferably, this element is made from a relatively soft material which may be rubber, synthetic rubber, a foam material which may be fabricated from the polymers identified above or from other materials. The occlusion element may also be made from metal, but a non-metal material is preferred for most uses.

Furthermore, a material may be added to the outside of the occlusion element which will promote scarring, typically by physical irritation of the fallopian tube tissue or by other scarring mechanisms which may include chemical compounds, to further insure the integrity of the occlusion of the fallopian tube.

Shape-memory metals or polymers are preferred for fabricating the fixation element 17. These shape-memory materials may be composites, e.g., polymers which contain particulate or other additives, such as carbon particles or fibers, and may be combinations of metal and polymer, such as a coated metal. The shape memory may be temperature dependent, i.e., actuated by heating or other energy input, or may be mechanical in nature. Such materials are well known to those skilled in the art.

Figure 9:
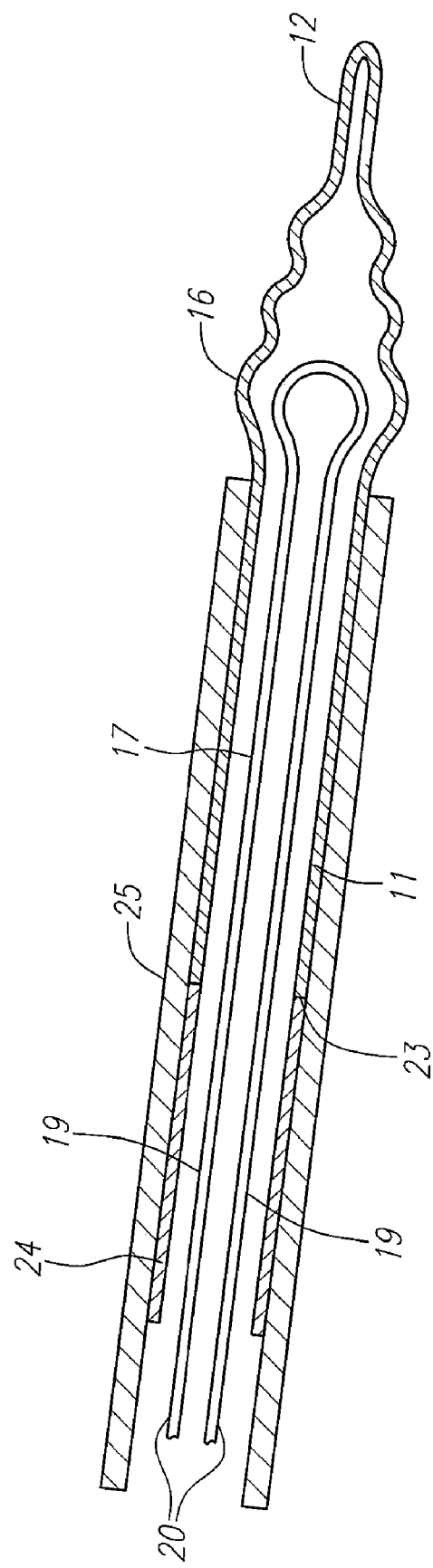
FIG. 9 is a schematic illustration of a portion of the deployment means used to deliver the occlusion device into the fallopian tube.

FIG. 9 is a schematic illustration of the delivery system of the present invention. As shown, inner tube 24 compresses the bowed portions 19 of the fixation element such that the bowed portions are aligned with the proximal portions 20. Outer sleeve 25 functions as a pusher element and is connected to a handle (not shown). The outer sleeve 25 is dimensioned so that it will fit in the additional lumen in a hysteroscope and, when pushed distally by applying force to the handle to which it is attached, will advance the occluding element into the fallopian tube. Once the desired location is achieved, outer sleeve 25 is removed. At this time, inner sleeve 24 which abuts the proximal end 23 of the occlusion element is also removed by pulling it in a proximal direction. When inner sleeve 24 is removed, bowed portion 19 of the fixation element will expand outwardly into the tissue of the fallopian tube to effectively hold the device in place.

FIGS. 10A-C are sequential schematic drawings which further illustrate delivery of the occlusion device. In these drawings, element 26 is a handle which slidably receives outer sleeve 25. When trigger 27 is pulled, it slides outer sleeve 25 proximally away from the occlusion device to deploy it in the fallopian tube. Inner sleeve 24 is then also moved proximally to release bowed portions 19 of the fixation element as shown in FIG. 10C.

Figure 11:
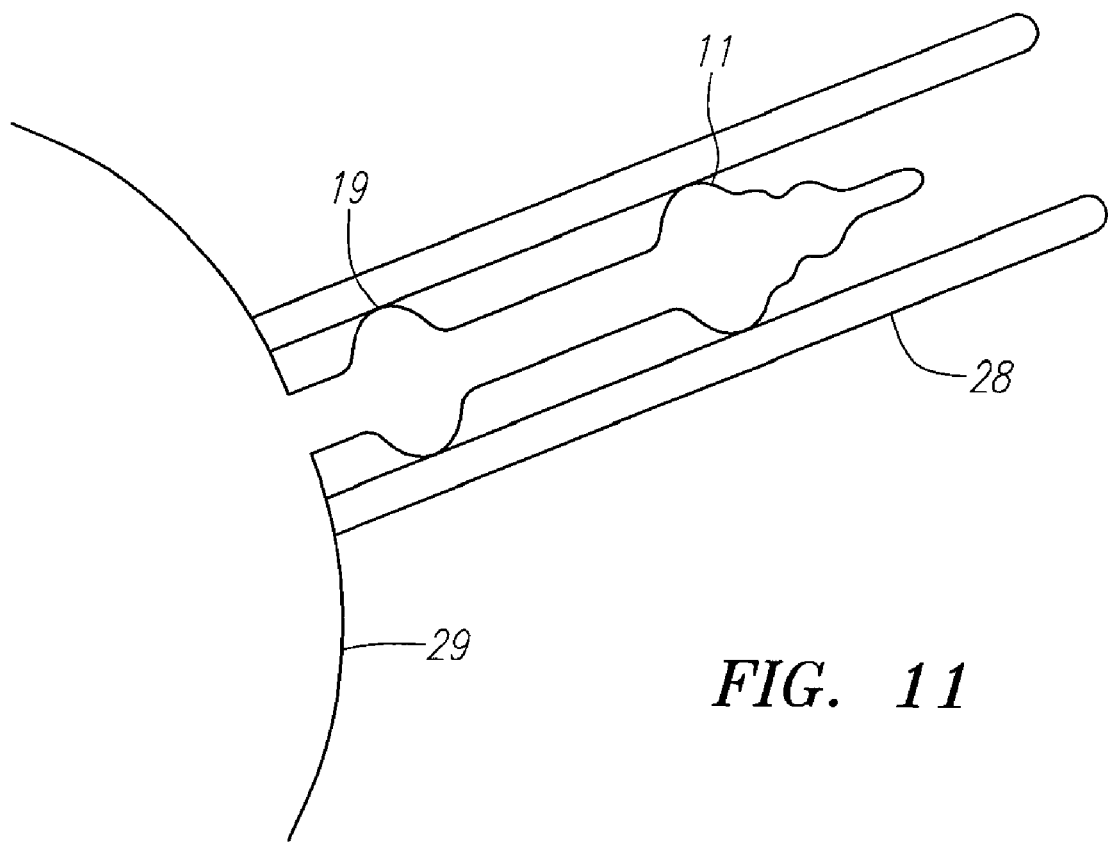
FIG. 11 is a schematic illustration which shows the occlusion device of FIG. 6 after it has been deployed in a fallopian tube.

FIG. 11 is a schematic illustration of the occlusion element 11 deployed in fallopian tube 28 with the bowed portion 19 of the fixation element engaged with the tissue of fallopian tube 28. In actual practice, the bowed portion 19 of the fixation element would penetrate the fallopian tube tissue and the occluder element would be large enough to cause the contour of the fallopian tube to be altered to be in a satisfactory degree of confirmation to the shape of the occluder device to assure effective occlusion.

The foregoing description of specific embodiments exemplifies the present invention and is but one embodiment thereof. Thus, it is to be understood that the scope of this invention is defined solely by the appended claims.

We claim:

1. In a device for occluding a body lumen or passageway, the improvement comprising a tubular member comprising a cap and a body, the body having an extended configuration when stressed and shorter configuration when unstressed, the body being provided with attachment members which are collapsed when the body is extended and expandable by unstressing the body, the cap having a lateral dimension larger than that of the body and adapted to substantially occlude said lumen, the body housing a plug and the cap having a through-hole, said unstressing being capable of shortening said body and moving said plug into said through-hole.

2. The device of claim 1 in combination with a delivery means comprising a grasper which engages said cap and a plunger which applies axial stress to said body through said through-hole.

3. In a device for occluding a fallopian tube, the improvement comprising an elongate member comprising a cap and a body, the cap having a configuration capable of occluding a fallopian tube and the body housing a plug, the body having an extended configuration when stressed and a shorter configuration when unstressed, the body being provided with retractable, laterally extending attachment members which are collapsed when the body is extended and which expand when stress is removed from the body, the cap having a lateral dimension larger than that of the body and being adapted to substantially occlude a fallopian tube, the body housing a plug and the cap having a through-hole, the removal of stress being capable of shortening said body and causing said plug to move into said through-hole thereby sealing it.

4. The device of claim 3, wherein said body is tubular and a lumen in said body is coaxial with the through-hole in said cap.

5. A method for occluding a fallopian tube comprising the steps of
    inserting into the lumen of a fallopian tube a stressed occlusion device comprising an elongate member having a cap and a tubular body, said cap having a lateral dimension larger than that of said body and configured to substantially occlude said lumen, said body being capable of being extended by applying stress, said body being provided with compressible attachment members adapted to expand laterally when the stress is removed from the body and having said attachment members in a compressed state, said body housing a plug and said cap having a through-hole,
    deploying said stressed occlusion device in said lumen such that said cap substantially occludes said lumen, and
    removing the stress from said body whereby the plug is moved into said through-hole and occludes it and the attachment means expand in a manner and engage the walls of said lumen.

6. The method of claim 5 wherein a stress on said body is applied axially.

7. A method for occluding a body lumen or passageway comprising the steps of:
    inserting into a desired body lumen a stressed occlusion device comprising an elongate member having a cap and a tubular body, said cap having a lateral dimension larger than that of the body, said body being capable of being extended by applying stress, said body being provided with compressible attachment members adapted to expand laterally when the stress is removed and having said attachment members in a compressed state, said body also housing a plug and said cap having a hole;
    deploying said stressed occlusion device in said lumen such that said cap substantially occludes said lumen, and
    removing the stress from said body whereby the plug is moved into said through-hole and occludes it and the attachment members expand and engage the walls of said lumen.

8. In a device for occluding a fallopian tube, the improvement comprising
    an elongate member having a proximal and distal end, comprising a cap in the region of its proximal end, and a tubular body, said cap having a larger lateral dimension than that of the body, said cap having a through-hole, a plug slidably housed in said body,
    said body having a longitudinally extended configuration when stressed in a longitudinal direction and a shorter configuration when unstressed,
    said body having expandable attachment members which are retracted when said body is stressed and which expand laterally when said body is unstressed,
    said plug being adapted to slide into said through-hole when stress is removed from the body, thereby occluding said through-hole.

* * * * *